United States Patent
Saito et al.

(10) Patent No.: US 7,709,432 B2
(45) Date of Patent: May 4, 2010

(54) SOLID SOAP COMPOSITION COMPRISING POLYSILXOXANE AND DIAMINE

(75) Inventors: Yoshinobu Saito, Osaka (JP); Daiji Nagahama, Osaka (JP); Shinya Yamasaki, Osaka (JP); Takahiro Okuda, Osaka (JP); Tetsuo Nishina, Osaka (JP)

(73) Assignee: P & PF Co., Ltd., Ibaraki-Shi (JP)

( * ) Notice: Subject to any disclaimer, the term of this patent is extended or adjusted under 35 U.S.C. 154(b) by 842 days.

(21) Appl. No.: 10/593,615

(22) PCT Filed: Mar. 10, 2005

(86) PCT No.: PCT/JP2005/004184

§ 371 (c)(1),
(2), (4) Date: Sep. 21, 2006

(87) PCT Pub. No.: WO2005/097965

PCT Pub. Date: Oct. 20, 2005

(65) Prior Publication Data

US 2007/0225195 A1    Sep. 27, 2007

(30) Foreign Application Priority Data

Mar. 30, 2004    (JP) .............................. 2004-100210

(51) Int. Cl.
*A61K 7/00*    (2006.01)

(52) U.S. Cl. ...................... 510/141; 510/147; 510/152; 510/153; 510/155

(58) Field of Classification Search ...................... None
See application file for complete search history.

(56) References Cited

U.S. PATENT DOCUMENTS 4,290,904 A * 9/1981 Poper et al. .................. 510/147

FOREIGN PATENT DOCUMENTS

| JP | 57-96099 | 6/1982 |
|----|----------|--------|
| JP | 63-122618 A | 5/1988 |
| JP | 02-273618 | 11/1990 |
| JP | 11-106331 | 4/1999 |
| JP | 2000-247892 | 9/2000 |
| JP | 2003-129094 | 5/2003 |
| JP | 2005-281596 | 9/2005 |

* cited by examiner

*Primary Examiner*—Necholus Ogden, Jr.
(74) *Attorney, Agent, or Firm*—Marvin A. Motsenbocker; Mots Law, PLLC

(57) ABSTRACT

A solid soap composition which comprises as essential ingredients a soap ingredient (a), a specific polyoxyalkylene-modified polysiloxane Co), and a tetrakis(2-hydroxyalkyl)ethylenediamine(c). It is a detergent with which makeup removal and ordinary face washing can be simultaneously conducted at a time. It lathers well and gives a fresh use feeling after washing. It can sufficiently remove not only foundations but acid pigments.

20 Claims, No Drawings

SOLID SOAP COMPOSITION COMPRISING POLYSILXOXANE AND DIAMINE

TECHNICAL FIELD

The present invention relates to a solid soap and a raw material composition thereof, and more specifically, relates to a solid soap and a raw material composition thereof for cleaning skin that can perform makeup removal at the same time during facial cleaning.

BACKGROUND ART

Made-up skin is cleaned in the following procedure: first, make-up cosmetic materials are mixed with a cleanser for removing makeup such as cleansing creams and cleansing oils containing a large amount of oil that is easily mixed with the make-up cosmetic materials, and removed by flushing with water or lukewarm water, then sebaceous matters and stains on the skin are removed together with oil of the cleanser remaining on the skin using a face cleaner such as soaps and cleansing foams. This two-step cleaning provides a clean feel after cleaning.

This two-step cleaning is necessary because a cleanser for removing makeup contains a large amount of oil, and thus even when rinsed with water or lukewarm water, the oil of the cleanser remains on the skin, so that a clean feel cannot be obtained after cleaning, and because it is impossible to sufficiently remove oil-based make-up cosmetic materials from the skin only with an ordinary face cleaner such as soaps and cleansing foams.

In accordance with recent change in the life style, there is a request for simplicity in cleaning made-up skin, and with respect to this request, face cleaners have been proposed that can perform makeup removal and ordinary facial cleaning at the same time in single facial cleaning. For example, Patent Document 1 discloses a cleaning agent containing polyoxyethylene glycerine fatty acid ester and polyoxyalkylene-modified polysiloxane, and Patent Document 2 discloses a skin cleaner containing polyoxyethylene diester, an anionic surfactant, an amphoteric surfactant, and polyoxyalkylene-modified methyl polysiloxane. All of these face cleaners are in either liquid form or gel form.

In the cleaning agents described above, mainly polyoxyalkylene-modified methyl polysiloxane removes make-up cosmetic materials, but when mixing this component, there is a problem in that the foaming property becomes insufficient and in that this component remains on skin after facial cleaning and thus a clean feel cannot be obtained after cleaning. Furthermore, although this component can remove make-up cosmetic materials such as cosmetic foundations, it cannot sufficiently remove make-up cosmetic materials that are acid pigments (such as lipsticks).

Patent Document 1: JP H05-75723B
Patent Document 2: JP H11-106331A

DISCLOSURE OF INVENTION

The prevent invention has been made in order to solve the problems described above, and it is an object thereof to provide a cleaning agent capable of performing makeup removal and ordinary facial cleaning at the same time in single facial cleaning, that has sufficient foaming property, that provides a clean feel after cleaning, and that can sufficiently remove not only cosmetic foundations but also acid pigments.

The inventors conducted in-depth research on the problems described above, and found that the problems described above are solved by providing a solid soap composition in which polyoxyalkylene-modified polysiloxane and a specific amine compound are mixed into a soap component, and as a result, the present invention has been achieved.

The present invention is directed to a solid soap composition comprising:

a soap component (a);

polyoxyalkylene-modified polysiloxane (b) that is expressed by formula (1) below,

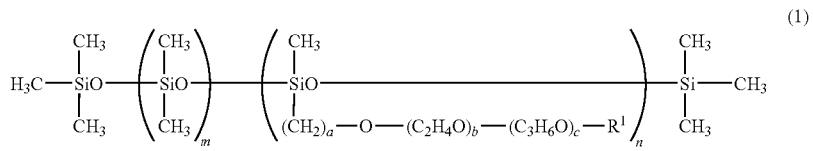

(where, R1 represents a hydrogen atom or an alkyl group having 1 to 5 carbon atoms, m represents an integer of 1 to 60, n represents an integer of 1 to 60, a represents an integer of 1 to 10, b represents an integer of 1 to 30, and c represents an integer of 0 to 30); and tetrakis (2-hydroxyalkyl) ethylene diamine (c) that is expressed by formula (2) below,

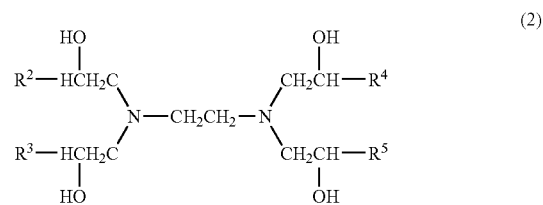

(where, R2 to R5 are the same or different and each independently represent a hydrogen atom or an alkyl group having 1 to 5 carbon atoms), as essential components.

In an embodiment of the present invention, it is preferable that the polyoxyalkylene-modified polysiloxane (b) of formula (1) is polyoxyethylene-modified polysiloxan. Furthermore, it is preferable that the tetrakis (2-hydroxyalkyl) ethylene diamine (c) of formula (2) is at least one selected from the group consisting of tetrakis (2-hydroxypropyl) ethylene diamine, and tetrakis (2-hydroxybutyl) ethylene diamine.

In an embodiment of the present invention, it is preferable to further contain a fatty acid ester-based nonionic surfactant (d). It is preferable that the fatty acid ester-based nonionic surfactant (d) is at least one selected from the group consisting of polyalkylene glycol difatty acid ester, trifatty acid glyceryl, and trifatty acid polyoxyalkylene glyceryl.

In an embodiment of the present invention, it is preferable to further contain an amphoteric surfactant (e) and a polyhydric alcohol (f). It is preferable that the amphoteric surfactant (e) is at least one selected from the group consisting of an imidazolinium betaine-based amphoteric surfactant, an amidoalkyl betaine-based amphoteric surfactant, and an alkyl betaine-based amphoteric surfactant. It is preferable that the polyhydric alcohol (f) is at least one selected from the group consisting of glycerin, diglycerine, 1,3-butylene glycol, propylene glycol, polyoxypropylene glyceryl ether, and polyoxypropylene diglyceryl ether.

In an embodiment of the present invention, it is preferable to further contain alkali ion water (g).

BEST MODE FOR CARRYING OUT THE INVENTION

Hereinafter, the present invention is described in detail. A solid soap composition according to the present invention contains a soap component (a), polyoxyalkylene-modified polysiloxane (b) of formula (1) above, and tetrakis (2-hydroxyalkyl) ethylene diamine (c) of formula (2) above, as essential components.

<Component (a)>

Examples of the soap component (a) used in the present invention include alkali salts of a higher fatty acid. Herein, the higher fatty acid is a saturated or unsaturated fatty acid having 8 to 24 carbon atoms, preferably having 12 to 18 carbon atoms, and may be either linear or branched. Specific examples thereof include saturated fatty acids such as lauric acid, myristic acid, palmitic acid, stearic acid, and isostearic acid; unsaturated fatty acids such as oleic acid; and mixtures thereof such as coconut oil fatty acid, palm oil fatty acid, palm kernel oil fatty acid, beef tallow fatty acid, and hardened beef tallow fatty acid. These fatty acids may be used alone or in combination of two or more types.

Furthermore, examples of the alkali include alkali metals such as sodium and potassium, alkaline-earth metals, alkanolamine, ammonium, and basic amino acids. These alkalis may be used alone or in combination of two or more types.

Examples of a preferable soap component include sodium laurate, sodium myristate, sodium palmitate, sodium stearate, sodium oleate, sodium isostearate, coconut oil fatty acid sodium, palm oil fatty acid sodium, and palm kernel oil fatty acid sodium.

In the solid soap composition according to the present invention, the content of the soap component (a) is preferably 20 to 40 wt %, and more preferably 25 to 35 wt %, with respect to the entire raw materials of the solid soap. When the content of this component is less than 20 wt %, the solidifying point becomes low, and thus the surface melts in long storage, so that the value as a product may be impaired. On the contrary, when the content of this component is more than 40 wt %, the transparency may be poor, and skin may have a tight feel after use.

<Component (b)>

The polyoxyalkylene-modified polysiloxane (b) used in the present invention is a compound that is expressed by formula (1) above. This polyoxyalkylene-modified polysiloxane (b) mainly plays a role to be mixed with and remove make-up cosmetic materials (in particular, cosmetic foundations), but also is advantageous in that the foaming property of the soap component (a) is not inhibited and in that if the composition is transparent, then the transparency thereof is not inhibited.

Furthermore, in formula (1) above, the "alkyl group having 1 to 5 carbon atoms" of R1 may be either linear or branched, and preferably has 1 to 3 carbon atoms. m is an integer of 1 to 60, preferably an integer of 5 to 30. n is an integer of 1 to 60, preferably an integer of 1 to 10. a is an integer of 1 to 10, preferably an integer of 1 to 5. b is an integer of 1 to 30, preferably an integer of 1 to 15. c is an integer of 0 to 30, preferably an integer of 0 to 15.

Examples of such polyoxyalkylene-modified polysiloxane (b) include copolymers of dimethyl polysiloxane and polyethylene glycol, and copolymers of dimethyl polysiloxane and polyoxyethylene polyoxypropylene glycol.

The polyoxyalkylene-modified polysiloxane (b) preferably has an HLB of 3 to 20, and more preferably 4 to 18. When the HLB is less than 3, the transparency or the foaming property may be poor. On the contrary, when the HLB is more than 20, an effect of removing make-up cosmetic materials may be insufficient.

The polyoxyalkylene-modified polysiloxane (b) may be used alone or in combination of two or more types.

In the present invention, among the examples of the polyoxyalkylene-modified polysiloxane (b), polyoxyethylene-modified polysiloxane (that is, c is 0) is preferably used in view of the hydrophilicity, and specific examples thereof include Silicone KF6011 (R1 is a methyl group, m is 5 to 10, n is 4 to 6, a is 3, and b is 9 to 13: produced by Shin-Etsu Chemical Co., Ltd.), Silicone SC9450 (R1 is a hydrogen atom, m is 50 to 60, n is 2 to 5, a is 3, and b is 8 to 10: produced by Shin-Etsu Chemical Co., Ltd.), and Silicone KF945 (R1 is a hydrogen atom, m is 20 to 30, n is 2 to 5, a is 3, and b is 2 to 5: produced by Shin-Etsu Chemical Co., Ltd.).

In the solid soap composition according to the present invention, the content of the polyoxyalkylene-modified polysiloxane (b) is preferably 1 to 15 wt %, and more preferably 2 to 10 wt %, with respect to the entire raw materials of the solid soap. When the content of this component is less than 1 wt %, an effect of removing make-up cosmetic materials may be insufficient. On the contrary, when the content of this component is more than 15 wt %, the solidifying property or the foaming property may be poor.

<Component (c)>

The tetrakis (2-hydroxyalkyl) ethylene diamine (c) used in the present invention is a compound that is expressed by formula (2) above. This tetrakis (2-hydroxyalkyl) ethylene diamine (c) mainly plays a role to be mixed with and remove make-up cosmetic materials (in particular, acid pigments such as lipsticks) together with the polyoxyalkylene-modified polysiloxane (b), but also is advantageous in that the foaming property of the soap component (a) is not inhibited and in that if the composition is transparent, then the transparency thereof is not inhibited.

In formula (2) above, the "alkyl group having 1 to 5 carbon atoms" of R2 to R5 may be either linear or branched, and preferably has 1 to 3 carbon atoms.

The tetrakis (2-hydroxyalkyl) ethylene diamine (c) may be used alone or in combination of two or more types.

In the present invention, among the examples of the tetrakis (2-hydroxyalkyl) ethylene diamine (c), tetrakis (2-hydroxypropyl) ethylene diamine (that is, all of R2 to R5 are methyl groups), and tetrakis (2-hydroxybutyl) ethylene diamine (that is, all of R2 to R5 are ethyl groups) are preferably used in view of their good effect of removing make-up cosmetic materials.

In the solid soap composition according to the present invention, the content of the tetrakis (2-hydroxyalkyl) ethylene diamine (c) is preferably 1 to 10 wt %, and more preferably 1 to 5 wt %, with respect to the entire raw materials of the solid soap. When the content of this component is less than 1 wt %, an effect of removing make-up cosmetic materials may be insufficient. On the contrary, when the content of this component is more than 10 wt %, the color or the odor may be changed.

Furthermore, in the solid soap composition according to the present invention, the total content of the polyoxyalkylene-modified polysiloxane (b) and the tetrakis (2-hydroxyalkyl) ethylene diamine (c) is preferably 3 to 15 wt %, and more preferably 4 to 10 wt %. Moreover, regarding the polyoxyalkylene-modified polysiloxane (b) and the tetrakis (2-hydroxyalkyl) ethylene diamine (c), the mixing ratio (weight ratio) of (b):(c) is preferably 10:1 to 1:10, and more preferably 3:1 to 1:3.

<Component (d)>

The solid soap composition according to the present invention preferably contains a fatty acid ester-based nonionic surfactant (d) in addition to the soap component (a), the polyoxyalkylene-modified polysiloxane (b), and the tetrakis (2-hydroxyalkyl) ethylene diamine (c). This fatty acid ester-based nonionic surfactant (d) is for being mixed with and removing make-up cosmetic materials together with the polyoxyalkylene-modified polysiloxane (b) and the tetrakis (2-hydroxyalkyl) ethylene diamine (c), but also can provide a moist feel after cleaning.

Examples of the fatty acid ester-based nonionic surfactant (d) used in the present invention include polyalkylene glycol difatty acid ester, trifatty acid glyceryl, trifatty acid polyoxyalkylene glyceryl, and polyoxyethylene hardened castor oil. Among these, polyalkylene glycol difatty acid ester, trifatty acid glyceryl, and trifatty acid polyoxyalkylene glyceryl are preferably used.

The polyalkylene glycol difatty acid ester is a compound that is expressed by formula (3) below, the trifatty acid glyceryl is a compound that is expressed by formula (4) below, and the trifatty acid polyoxyalkylene glyceryl is a compound that is expressed by formula (5) below.

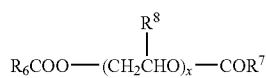

(3)

(where, R6 and R7 are the same or different and each independently represent an alkyl group having 8 to 22 carbon atoms or an alkenyl group having 8 to 22 carbon atoms, R8 represents a hydrogen atom or an alkyl group having 1 to 5 carbon atoms, and x represents an integer of 1 to 40.)

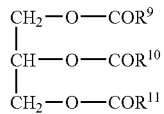

(4)

(where, R9 to R11 are the same or different and each independently represent an alkyl group having 8 to 22 carbon atoms or an alkenyl group having 8 to 22 carbon atoms.)

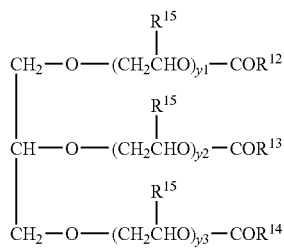

(5)

(where, R12 to R14 are the same or different and each independently represent an alkyl group having 10 to 20 carbon atoms or an alkenyl group having 10 to 20 carbon atoms, R15 represents a hydrogen atom or an alkyl group having 1 to 5 carbon atoms, and y1 to y3 are the same or different and each represent an integer of 1 to 80.)

In formula (3) above, the "alkyl group having 8 to 22 carbon atoms" of R6 and R7 may be either linear or branched, and preferably has 10 to 20 carbon atoms. Furthermore, the "alkenyl group having 8 to 22 carbon atoms" of R6 and R7 may be either linear or branched, and preferably has 10 to 20 carbon atoms. The "alkyl group having 1 to 5 carbon atoms" of R8 may be either linear or branched, and preferably has 1 to 3 carbon atoms. x is an integer of 1 to 40, preferably an integer of 2 to 20.

In formula (4) above, the "alkyl group having 8 to 22 carbon atoms" of R9 to R11 may be either linear or branched, and preferably has 10 to 20 carbon atoms. Furthermore, the "alkenyl group having 8 to 22 carbon atoms" of R9 to R11 may be either linear or branched, and preferably has 10 to 20 carbon atoms.

In formula (5) above, the "alkyl group having 10 to 20 carbon atoms" of R12 to R14 may be either linear or branched, and preferably has 14 to 20 carbon atoms. Furthermore, the "alkenyl group having 10 to 20 carbon atoms" of R12 to R14 may be either linear or branched, and preferably has 14 to 20 carbon atoms. The "alkyl group having 1 to 5 carbon atoms" of R15 may be either linear or branched, and preferably has 1 to 3 carbon atoms. y1 to y3 are integers of 1 to 80, preferably integers of 10 to 60.

As preferable polyalkylene glycol difatty acid ester, polyethylene glycol difatty acid ester (that is, R8 is a hydrogen atom) is preferably used, and specific examples thereof include polyethylene glycol diisostearic acid ester, polyethylene glycol dioleic acid ester, polyethylene glycol distearic acid ester, and polyethylene glycol dilauric acid ester.

Examples of preferable trifatty acid glyceryl include tri(2-ethylhexanoic acid) glyceryl, triisostearic acid glyceryl, tri (caprylic-capric acid) glyceryl, and hydrogenated tri-coconut oil fatty acid glyceryl.

As preferable trifatty acid polyoxyalkylene glyceryl, trifatty acid polyoxyethylene glyceryl (that is, R15 is a hydrogen atom) is preferably used, and specific examples thereof include triisostearic acid polyoxyethylene glyceryl, and tristearic acid polyoxyethylene glyceryl.

The fatty acid ester-based nonionic surfactant (d) preferably has an HLB of 3 to 15, and more preferably 4 to 10. When the HLB is less than 3, the solubility is poor, and thus the appearance may become bad. On the contrary, when the HLB is more than 15, an effect of removing make-up cosmetic materials may be insufficient.

The fatty acid ester-based nonionic surfactant (d) may be used alone or in combination of two or more types.

In the solid soap composition according to the present invention, the content of the fatty acid ester-based nonionic surfactant (d) is preferably 1 to 10 wt %, and more preferably 1 to 5 wt %, with respect to the entire raw materials of the solid soap. When the content of this component is less than 1 wt %, an effect of removing make-up cosmetic materials may be insufficient, and a moist feel after cleaning may be insufficient. On the contrary, when the content of this component is more than 10 wt %, skin may have a sticky feel after cleaning.

Furthermore, regarding the polyoxyalkylene-modified polysiloxane (b) and the fatty acid ester-based nonionic surfactant (d), the mixing ratio (weight ratio) of (b):(d) is preferably 4:1 to 1:4, and more preferably 3:1 to 1:3. Moreover, regarding the tetrakis (2-hydroxyalkyl) ethylene diamine (c) and the fatty acid ester-based nonionic surfactant (d), the mixing ratio (weight ratio) of (c):(d) is preferably 4:1 to 1:4, and more preferably 2:1 to 1:2.

The solid soap composition according to the present invention preferably contains an amphoteric surfactant (e) and a polyhydric alcohol (f) in addition to the components described above. When the amphoteric surfactant (e) and the polyhydric alcohol (f) are mixed, together with the polyoxyalkylene-modified polysiloxane (b) and the fatty acid ester-based nonionic surfactant (d) that are nonionic surfactants, into the solid soap composition having the soap component (a) as a main component, a transparent composition having a beautiful appearance is obtained. Furthermore, when the amphoteric surfactant (e) is mixed, the foaming property of the composition is improved.

<Component (e)>

Examples of the amphoteric surfactant (e) used in the present invention include an imidazolinium betaine-based amphoteric surfactant that is expressed by formula (6) below, an amidoalkyl betaine-based amphoteric surfactant that is expressed by formula (7) below, and an alkyl betaine-based amphoteric surfactant that is expressed by formula (8) below. These amphoteric surfactants may be used alone or in combination of two or more types.

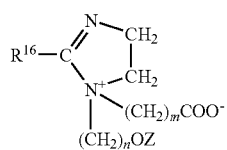
(6)

(where, R16 represents an alkyl group or alkenyl group having 7 to 21 carbon atoms, n and m are the same or different and each represent an integer of 1 to 3, Z represents a hydrogen atom or $(CH_2)pCOOY$ (where, p is an integer of 1 to 3, Y is an alkali metal, an alkaline-earth metal, or organic amine).)

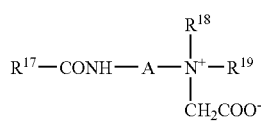
(7)

(where, R17 represents an alkyl group or alkenyl group having 7 to 21 carbon atoms, R18 and R19 are the same or different and each independently represent a lower alkyl group, and A represents a lower alkylene group.)

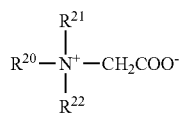
(8)

(where, R20 represents an alkyl group or alkenyl group having 8 to 22 carbon atoms, and R21 and R22 are the same or different and each independently represent a lower alkyl group.)

In formula (6), the "alkyl group having 7 to 21 carbon atoms" of R16 may be either linear or branched, and preferably has 7 to 17 carbon atoms. Furthermore, the "alkenyl group having 7 to 21 carbon atoms" of R16 may be either linear or branched, and preferably has 7 to 17 carbon atoms. Moreover, examples of the "alkali metal" of Y include sodium and potassium, examples of the "alkaline-earth metal" include calcium and magnesium, and examples of the "organic amine" include monoethanolamine, diethanolamine, and triethanolamine.

Specific examples of the imidazolinium betaine-based amphoteric surfactant of formula (6) include 2-undecyl-N-carboxymethyl-N-hydroxyethyl imidazolinium betaine (synthesized using a lauric acid, also referred to as "lauroyl imidazolinium betaine"), 2-heptadecyl-N-carboxymethyl-N-hydroxyethyl imidazolinium betaine (synthesized using a stearic acid, also referred to as "stearoyl imidazolinium betaine"), and 2-alkyl or alkenyl-N-carboxymethyl-N-hydroxyethyl imidazolinium betaine (a mixture in which R16 is C7 to C17, also referred to as "cocoil imidazolinium betaine") synthesized using a coconut oil fatty acid.

In formula (7), the "alkyl group having 7 to 21 carbon atoms" and the "alkenyl group having 7 to 21 carbon atoms" of R17 are similar to those of R16 of formula (6). Furthermore, the "lower alkyl group" of R18 and R19 is a linear or branched alkyl group preferably having 1 to 3 carbon atoms. Moreover, the "lower alkylene group" of A is a linear or branched alkylene group preferably having 3 to 5 carbon atoms.

Specific examples of the amidoalkyl betaine-based amphoteric surfactant of formula (7) include amide propyl betaine-based, for example, coconut oil fatty acid amide propyl dimethyl aminoacetic acid betaine (a mixture in which R17 is C7 to C17).

In formula (8), the "alkyl group having 8 to 22 carbon atoms" of R20 may be either linear or branched, and preferably has 8 to 18 carbon atoms. Furthermore, the "alkenyl group having 8 to 22 carbon atoms" of R20 may be either linear or branched, and preferably has 8 to 18 carbon atoms. Moreover, the "lower alkyl group" of R21 and R22 are similar to those of R18 and R19 of formula (7).

Specific examples of the alkyl betaine-based amphoteric surfactant of formula (8) include lauryl dimethyl aminoacetic acid betaine, and alkyl or alkenyldimethyl aminoacetic acid betaine (a mixture in which R20 is C8 to C18) synthesized using a coconut oil fatty acid.

Among the amphoteric surfactants described above, the imidazolinium betaine-based amphoteric surfactant of formula (6) above, in particular cocoil imidazolinium betaine is preferably used.

In the solid soap composition according to the present invention, the content of the amphoteric surfactant (e) is preferably 2 to 10 wt %, and more preferably 4 to 8 wt %, with respect to the entire raw materials of the solid soap. When the content of this component is less than 2 wt %, the transparency and the foaming property may be poor. On the contrary, when the content of this component is more than 10 wt %, the color or the odor may be changed.

<Component (f)>

Examples of the polyhydric alcohol (f) used in the present invention include, alkylene glycols such as ethylene glycol, propylene glycol, 1,3-butylene glycol, diethylene glycol, dipropylene glycol, polyethylene glycol, and polypropylene glycol;

glycerins such as glycerin, diglycerine, and polyglycerin;

glycerin derivatives such as polyoxypropylene glyceryl ether, polyoxypropylene diglyceryl ether, polyoxypropylene polyglyceryl ether, polyoxyethylene polyoxypropylene glyceryl ether, polyoxyethylene polyoxypropylene diglyceryl ether, and polyoxyethylene polyoxypropylene polyglyceryl ether;

saccharides such as sucrose, trehalose, fructose, and maltose; and sugar alcohols such as sorbitol, erythritol, xylitol, and maltitol. Among these, glycerin, diglycerine, 1,3-butylene glycol, propylene glycol, polyoxypropylene glyceryl ether, and polyoxypropylene diglyceryl ether are preferably used.

These examples of the polyhydric alcohol (f) may be used alone or in combination of two or more types.

In the solid soap composition according to the present invention, the content of the polyhydric alcohol (f) is preferably 5 to 45 wt %, and more preferably 15 to 35 wt %, with respect to the entire raw materials of the solid soap. When the content of this component is less than 5 wt %, the component may not be uniformly solidified. On the contrary, when the content of this component is more than 45 wt %, the component is not solidified and stays in liquid form.

<Component (g)>

The solid soap composition according to the present invention preferably contains alkali ion water (g) in addition to the components described above. When this alkali ion water (g) is mixed, the solid soap composition according to the present invention has an improved osmotic force to make-up cosmetic materials, and thus an effect of removing make-up cosmetic materials is improved.

There is no specific limitation regarding the alkali ion water (g) used in the present invention as long as it is alkali ion water obtained by electrolyzing water, but "Multi-cleaner S-100" and "Multi-cleaner GE-100" (both are sold by Nisseki Corporation) for example are preferably used.

In the solid soap composition according to the present invention, the alkali ion water (g) preferably has a pH of 8 to 13, and more preferably 10 to 13 in view of an effect of removing makeup.

In the solid soap composition according to the present invention, the content of the alkali ion water (g) is preferably 0.1 to 20 wt %, and more preferably 1 to 10 wt %, with respect to the entire raw materials of the solid soap. When the content of this component is less than 0.1 wt %, an effect of removing make-up cosmetic materials may not be improved. On the contrary, when the content of this component is more than 20 wt %, the cost is increased, and thus it is disadvantageous in an economic point of view.

Following components can be optionally mixed into the soap composition according to the present invention within a range in which the effects described above are not impaired. Examples of these optional components include bactericidal substances such as trichlorocarbanilide, hinokitiol, and sulfur; moisturizing agents such as pyrrolidone carboxylic acid, sodium pyrrolidone carboxylate, sodium hyaluronate, hyaluronic acid, and polyoxyethylene alkyl glucoside ether; oils; aroma chemicals; dyes; chelating agents such as edetate trisodium dehydrate; ultraviolet absorbers; antioxidants; natural extracts such as glycyrrhetinic acid dipotassium, plantain essence, lecithin, saponin, aloe, phellodendri cortex, and chamomile; nonionic, cationic, or anionic water-soluble polymers; usability improvers such as lactate; and foaming property improvers such as alkyl ether sodium carboxylate, alkyl disodium sulfosuccinate, alkyl sodium isethionate, polyoxyethylene alkyl sodium sulphate, acyl methyl taurine, acyl sodium glutamate, and acyl sodium sarcosinate.

Furthermore, into the solid soap composition according to the present invention, water is mixed within a range of 7 wt % or less including the alkali ion water (g), and alcohol is mixed within a range of 10 wt % or less, in order to sufficiently mix and dissolve the entire components. In the solid soap composition according to the present invention, the entire raw materials of the solid soap are taken as 100 wt % including these water and alcohol.

A solid soap is obtained from the solid soap composition according to the present invention by applying general methods such as a framing method and a milling method to the mixture of the components described above. A solid soap after molding becomes a complete product when a predetermined maturing period has passed. During this maturing period, most of alcohol mixed in the solid soap composition volatilizes, so that irritation caused by the solid soap is made smaller, thereby completing the product. The end of the maturing period can be determined-based on change in the volume of the solid soap caused by volatilization of alcohol, ion exchange water or other components, and more specifically, it is determined as appropriate at a point during a process where the volume of these volatilizing components, that is, the volume of 10% to 20% of the entire composition is reduced.

The solid soap composition according to the present invention contains the soap component (a), the polyoxyalkylene-modified polysiloxane (b) of formula (1) above, and the tetrakis (2-hydroxyalkyl) ethylene diamine (c) of formula (2) above, as essential components. With this composition, by mixing both the polyoxyalkylene-modified polysiloxane (b) and the tetrakis (2-hydroxyalkyl) ethylene diamine (c), not only cosmetic foundations but also make-up cosmetic materials that are acid pigments can be sufficiently removed. Furthermore, even when these components are mixed, the foaming property is sufficient because the soap component (a) is mixed. Moreover, due to the cleaning power the soap component (a), these components hardly remain on skin, and thus a clean feel can be provided after cleaning. Thus, with the solid soap composition according to the present invention, it is possible to provide a solid soap that can sufficiently remove not only cosmetic foundations but also make-up cosmetic materials that are acid pigments, and that can provide a clean feel after cleaning.

EXAMPLES

Hereinafter, the present invention is described in more detail by way of examples, but the present invention is not limited to these examples.

Examples 1 to 6 and Comparative Examples 1 to 4

Solid soaps of Examples 1 to 6 and Comparative Examples 1 to 6 were produced from the solid soap compositions with formulations listed in Table 1. It should be noted that in Table 1, the mixing amounts of the components are shown in wt %.

TABLE 1

|  | Examples | | | | | | Comparative Examples | | | |
| --- | --- | --- | --- | --- | --- | --- | --- | --- | --- | --- |
|  | 1 | 2 | 3 | 4 | 5 | 6 | 1 | 2 | 3 | 4 |
| sodium laurate | 7 | 7 | 7 | 7 | 8 | 6 | 7 | 7 | 7 | 7 |
| sodium myristate | 5 | 5 | 5 | 5 | 6 | 4 | 5 | 5 | 5 | 5 |
| sodium palmitate | 10 | 10 | 10 | 10 | 11 | 9 | 10 | 10 | 10 | 10 |
| sodium stearate | 1 | 1 | 1 | 1 | 2 | — | 1 | 1 | 1 | 1 |
| sodium oleate | 7 | 7 | 7 | 7 | 8 | 6 | 7 | 7 | 7 | 7 |

TABLE 1-continued

|  | Examples | | | | | | Comparative Examples | | | |
| --- | --- | --- | --- | --- | --- | --- | --- | --- | --- | --- |
|  | 1 | 2 | 3 | 4 | 5 | 6 | 1 | 2 | 3 | 4 |
| Silicone KF6011 | 5 | 5 | — | 5 | 6 | 8 | — | — | 5 | — |
| Silicone SC9450 | — | — | 5 | — | — | — | — | — | — | 5 |
| methyl polysiloxane | — | — | — | — | — | — | — | 5 | — | — |
| tetrakis (2-hydroxypropyl) ethylene diamine | 3 | 3 | 3 | — | 4 | — | 3 | 3 | — | — |
| tetrakis (2-hydroxybutyl) ethylene diamine | — | — | — | 3 | — | 3 | — | — | — | — |
| triethanolamine | — | — | — | — | — | — | — | — | — | 3 |
| diisostearic acid polyethylene glycol (X = 12) | 3 | 3 | 3 | 3 | — | 4 | 3 | 3 | 3 | 3 |
| tri(2-ethylhexanoic acid) glyceryl | — | — | — | — | 5 | — | — | — | — | — |
| coconut oil fatty acid imidazolinium betaine (30%) | 20 | 20 | 20 | 20 | 20 | 20 | 20 | 20 | 20 | 20 |
| glycerine | 13 | 13 | 13 | 13 | 7 | 14 | 18 | 13 | 16 | 13 |
| sugar | 10 | 10 | 10 | 10 | 7 | 10 | 10 | 10 | 10 | 10 |
| S-100 (alkali ion water) | — | 2 | 2 | 2 | 2 | 2 | 2 | 2 | 2 | 2 |
| edetate | 0.1 | 0.1 | 0.1 | 0.1 | 0.1 | 0.1 | 0.1 | 0.1 | 0.1 | 0.1 |
| olive oil | 0.1 | 0.1 | 0.1 | 0.1 | 0.1 | 0.1 | 0.1 | 0.1 | 0.1 | 0.1 |
| ion exchange water | 6.8 | 4.8 | 4.8 | 4.8 | 4.8 | 4.8 | 4.8 | 4.8 | 4.8 | 4.8 |
| alcohol | 9 | 9 | 9 | 9 | 9 | 9 | 9 | 9 | 9 | 9 |
| total | 100 | 100 | 100 | 100 | 100 | 100 | 100 | 100 | 100 | 100 |
| solidifying property | B | B | B | B | B | B | B | B | B | B |
| transparency | B | B | B | B | B | B | D | D | B | B |
| foaming property | B | B | B | B | B | B | D | D | B | B |
| lipstick cleaning efficiency | B | A | A | A | A | A | C | D | D | D |
| FD cleaning efficiency | B | A | A | A | A | A | D | D | C | C |
| makeup cleaning effect | B | A | A | A | A | B | C | D | C | C |
| feel after use | B | B | B | B | A | A | B | B | B | B |

An evaluation test was conducted following the method below on the solid soaps obtained in Examples 1 to 6 and Comparative Examples 1 to 6. The results are shown in Table 1.

<Evaluation Method>

1. Solidifying Property

An evaluation was conducted-based on the following criteria concerning three grades.

B: the material is in a solid state as a whole.

C: the material is in a solid state but soft as a whole.

D: the material cannot be in a solid state as a whole.

2. Transparency

Each sample was cut into a piece with a thickness of 20 mm, and placed on a 26-point printed character, and an evaluation was conducted-based on the following criteria concerning four grades.

A: the character can be read clearly.

B: the character can be read.

C: the character can be barely read.

D: the character cannot be read.

3. Foaming Property 100 women (20 to 40 years old) conducted a use test in a similar manner to that with ordinary facial cleaning soaps, and an evaluation was conducted-based on the following criteria concerning four grades.

A: when 75 to 100 people feel that foaming property is good.

B: when 50 to 74 people feel that foaming property is good.

C: when 25 to 49 people feel that foaming property is good.

D: when 0 to 24 people feel that foaming property is good.

4. Lipstick Cleaning Efficiency

An artificial leather sheet (Mayfair #5000 white, produced by Kyowaseikan CO., LTD) was cut into pieces of 3.0 cm×3.0 cm, and 0.03 g of lipstick (PN Lip Perfect 21 produced by Shiseido Company, Limited) was uniformly applied thereon using a doctor blade (thickness: 0.1 μm). These sheets on which the lipstick was applied were dried at 25° C. for 24 hours, and thus sample sheets were obtained. Apart from this, each soap was dissolved in artificial hard water (70 ppm), and thus a soap solution of 30 wt % was prepared. L1, a1, and b1 were measured by observing four artificial leather sheets on which no material was applied with a microscope [50×, HI-SCOPE (COMPACT MICRO VISION SYSTEM: MODEL KH-2000)]. Also, L2, a2, and b2 were measured by observing the four sample sheets on which the lipstick was applied in a similar manner with the microscope (50×). Next, these sheets were set on a Sutherland friction testing machine (Testing machine Y.S.S), 0.5 ml of the 30 wt % soap solution (temperature 40° C.) was dropped thereon, and then the sheets were rubbed back and forth 20 times at a weight of 900 g. Subsequently, these sheets were washed with running water, and then dried on filter paper in a constant temperature bath at 25° C. for 12 hours. L3, a3, and b3 were measured by observing these sheets again with the microscope (50×). Then, based on equations below, the cleaning efficiency was calculated, and an evaluation was conducted-based on the following criteria concerning four grades.

$$\Delta E1 = [(L2-L1)2 + (a2-a1)2 + (b2-b1)2]^{1/2}$$

$$\Delta E2 = [(L3-L1)2 + (a3-a1)2 + (b3-b1)2]^{1/2}$$

$$\text{cleaning efficiency} = (1 - \Delta E2/\Delta E1) \times 100$$

L: brightness, a: vividness, b: hue

A: the cleaning efficiency is 75% or more.

B: the cleaning efficiency is 50% or more and less than 75%.

C: the cleaning efficiency is 25% or more and less than 49%.

D: the cleaning efficiency is less than 25%.

5. Cosmetic Foundation Cleaning Efficiency

In the method for testing the lipstick cleaning efficiency, a test was conducted in the same manner except that cosmetic foundations (Optune Liquid Foundation produced by Shiseido Company, Limited) was used instead of 0.03 g of the lipstick (PN Lip Perfect 21 produced by Shiseido Company, Limited), and an evaluation was conducted-based on the following criteria concerning four grades.

A: the cleaning efficiency is 75% or more.

B: the cleaning efficiency is 50% or more and less than 75%.

C: the cleaning efficiency is 25% or more and less than 49%.

D: the cleaning efficiency is less than 25%.

6. Makeup Cleaning Effect 100 women (20 to 40 years old) conducted a use test in a similar manner to that with ordinary facial cleaning soaps, and an evaluation was conducted-based on the following criteria concerning four grades.

A: when 75 to 100 people feel that makeup has been removed well.

B: when 50 to 74 people feel that makeup has been removed well.

C: when 25 to 49 people feel that makeup has been removed well.

D: when 0 to 24 people feel that makeup has been removed well.

7. Feel After Use 100 women (20 to 40 years old) conducted a use test in a similar manner to that with ordinary facial cleaning soaps, and an evaluation was conducted-based on the following criteria concerning four grades.

A: when 75 to 100 people feel that a moist feel is obtained after cleaning.

B: when 50 to 74 people feel that a moist feel is obtained after cleaning.

C: when 25 to 49 people feel that a moist feel is obtained after cleaning.

D: when 0 to 24 people feel that a moist feel is obtained after cleaning.

INDUSTRIAL APPLICABILITY

The solid soap composition according to the present invention can perform makeup removal at the same time during facial cleaning, and thus made-up skin can be cleaned sufficiently in single facial cleaning, so that it serves as a very convenient solid soap composition for cleaning skin.

The invention claimed is:

1. A solid soap composition comprising:
   a soap component (a);
   polyoxyalkylene-modified polysiloxane (b) that is expressed by formula (1) below,

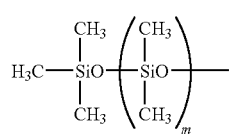

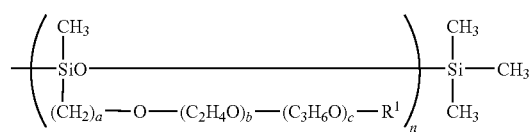

(1)

(where, R1 represents a hydrogen atom or an alkyl group having 1 to 5 carbon atoms, m represents an integer of 1 to 60, n represents an integer of 1 to 60, a represents an integer of 1 to 10, b represents an integer of 1 to 30, and c represents an integer of 0 to 30); and tetrakis (2-hydroxyalkyl) ethylene diamine (c) that is expressed by formula (2) below,

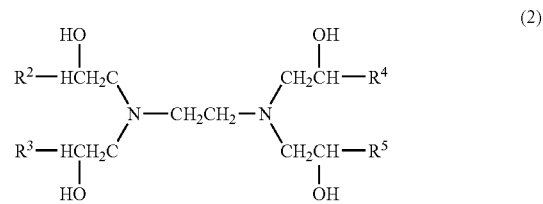

(2)

(where, R2 to R5 are the same or different and each independently represent a hydrogen atom or an alkyl group having 1 to 5 carbon atoms), as essential components.

2. The solid soap composition according to claim 1, wherein the polyoxyalkylene-modified polysiloxane (b) of formula (1) is polyoxyethylene-modified polysiloxan.

3. The solid soap composition according to claim 1, wherein the tetrakis (2-hydroxyalkyl)ethylene diamine (c) of formula (2) is at least one selected from the group consisting of tetrakis (2-hydroxypropyl)ethylene diamine, and tetrakis (2-hydroxybutyl)ethylene diamine.

4. The solid soap composition according to claim 1, further comprising a fatty acid ester-based nonionic surfactant (d).

5. The solid soap composition according to claim 4, wherein the fatty acid ester-based nonionic surfactant (d) is at least one selected from the group consisting of polyalkylene glycol difatty acid ester, trifatty acid glyceryl, and trifatty acid polyoxyalkylene glyceryl.

6. The solid soap composition according to claim 1, further comprising an amphoteric surfactant (e) and a polyhydric alcohol (f).

7. The solid soap composition according to claim 6, wherein the amphoteric surfactant (e) is at least one selected from the group consisting of an imidazolinium betaine-based amphoteric surfactant, an amidoalkyl betaine-based amphoteric surfactant, and an alkyl betaine-based amphoteric surfactant.

8. The solid soap composition according to claim 6, wherein the polyhydric alcohol (f) is at least one selected from the group consisting of glycerin, diglycerine, 1,3-butylene glycol, propylene glycol, polyoxypropylene glyceryl ether, and polyoxypropylene diglyceryl ether.

9. The solid soap composition according to claim 1, further comprising alkali ion water (g).

10. A solid soap that is formed when a predetermined maturing period has passed after molding the solid soap composition according to claim 1 into a solid soap by applying a framing method or a milling method.

11. A solid soap composition comprising:
    a soap component (a);
    polyoxyalkylene-modified polysiloxane (b) that is expressed by formula (1) below,

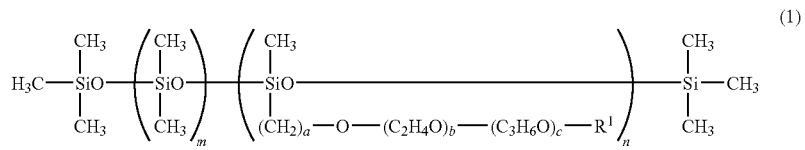

(where, R1 represents a hydrogen atom or an alkyl group having 1 to 5 carbon atoms, m represents an integer of 1 to 60, n represents an integer of 1 to 60, a represents an integer of 1 to 10, b represents an integer of 1 to 30, and c represents an integer of 0 to 30); and tetrakis (2-hydroxyalkyl)ethylene diamine (c) that is expressed by formula (2) below,

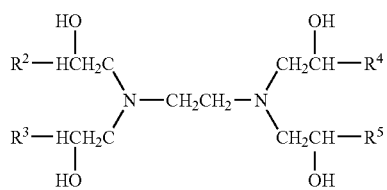

(where, R2 to R5 are the same or different and each independently represent a hydrogen atom or an alkyl group having 1 to 5 carbon atoms.

12. The solid soap composition according to claim 11, wherein the polyoxyalkylene-modified polysiloxane (b) of formula (1) is polyoxyethylene-modified polysiloxan.

13. The solid soap composition according to claim 11, wherein the tetrakis (2-hydroxyalkyl)ethylene diamine (c) of formula (2) is at least one selected from the group consisting of tetrakis (2-hydroxypropyl)ethylene diamine, and tetrakis (2-hydroxybutyl)ethylene diamine.

14. The solid soap composition according to claim 11, further comprising a fatty acid ester-based nonionic surfactant (d).

15. The solid soap composition according to claim 14, wherein the fatty acid ester-based nonionic surfactant (d) is at least one selected from the group consisting of polyalkylene glycol difatty acid ester, trifatty acid glyceryl, and trifatty acid polyoxyalkylene glyceryl.

16. The solid soap composition according to claim 11, further comprising an amphoteric surfactant (e) and a polyhydric alcohol (f).

17. The solid soap composition according to claim 16, wherein the amphoteric surfactant (e) is at least one selected from the group consisting of an imidazolinium betaine-based amphoteric surfactant, an amidoalkyl betaine-based amphoteric surfactant, and an alkyl betaine-based amphoteric surfactant.

18. The solid soap composition according to claim 16, wherein the polyhydric alcohol (f) is at least one selected from the group consisting of glycerin, diglycerine, 1,3-butylene glycol, propylene glycol, polyoxypropylene glyceryl ether, and polyoxypropylene diglyceryl ether.

19. The solid soap composition according to claim 11, further comprising alkali ion water (g).

20. A solid soap that is formed when a predetermined maturing period has passed after molding the solid soap composition according to claim 11 into a solid soap by applying a framing method or a milling method.

* * * * *